United States Patent
Bette et al.

(10) Patent No.: US 9,150,673 B2
(45) Date of Patent: Oct. 6, 2015

(54) PROCESS FOR PREPARING (METH)ACRYLIC ESTERS

(75) Inventors: Virginie Bette, Mannheim (DE); Matthias Dust, Ludwigshafen (DE); Jochen Petzoldt, Weisenheim am Berg (DE); Uwe Meisenburg, Mannheim (DE); Andrea Misske, Speyer (DE); Hermann Bergmann, Mannheim (DE)

(73) Assignee: BASF SE, Ludwigshafen (DE)

( * ) Notice: Subject to any disclaimer, the term of this patent is extended or adjusted under 35 U.S.C. 154(b) by 371 days.

(21) Appl. No.: 13/543,032

(22) Filed: Jul. 6, 2012

(65) Prior Publication Data

US 2013/0178592 A1   Jul. 11, 2013

Related U.S. Application Data

(60) Provisional application No. 61/504,727, filed on Jul. 6, 2011.

(51) Int. Cl.
| | |
|---|---|
| *C07C 67/02* | (2006.01) |
| *C08F 20/06* | (2006.01) |
| *C07C 67/03* | (2006.01) |
| *C07D 233/32* | (2006.01) |

(52) U.S. Cl.
CPC .................. *C08F 20/06* (2013.01); *C07C 67/03* (2013.01); *C07D 233/32* (2013.01)

(58) Field of Classification Search
CPC ........................................................ C07C 67/03
See application file for complete search history.

(56) References Cited

U.S. PATENT DOCUMENTS

| | | | |
|---|---|---|---|
| 7,528,278 B2 | 5/2009 | Benderly et al. | |
| 2005/0203211 A1 | 9/2005 | Gebhard | |
| 2006/0173191 A1 | 8/2006 | Curtis | |
| 2013/0090492 A1 * | 4/2013 | Goossens et al. | 558/275 |

FOREIGN PATENT DOCUMENTS

| | | |
|---|---|---|
| DE | 27 44 641 | 4/1979 |
| EP | 1 236 994 A2 | 9/2002 |
| EP | 1 574 533 A1 | 9/2005 |
| EP | 1686118 A1 * | 1/2006 |
| EP | 1 686 118 A1 | 8/2006 |
| WO | WO 2006/012980 A1 | 2/2006 |

OTHER PUBLICATIONS

International Search Report Issued Nov. 12, 2012 in PCT/EP2012/063073.

* cited by examiner

*Primary Examiner* — Paul A Zucker
(74) *Attorney, Agent, or Firm* — Oblon, McClelland, Maier & Neustadt, L.L.P.

(57) ABSTRACT

The invention relates to a process for preparing (meth)acrylic esters by esterifying (meth)acrylic acid or transesterifying at least one (meth)acrylic ester with at least one compound comprising at least one OH group in the presence of a heterogeneous catalyst comprising at least one inorganic salt, wherein the esterification or transesterification is performed in the presence of 300 to 3000 ppm of water based on the total weight of the reaction mixture.

13 Claims, No Drawings

PROCESS FOR PREPARING (METH)ACRYLIC ESTERS

The present invention relates to a process for preparing (meth)acrylic esters by esterifying (meth)acrylic acid or transesterifying at least one (meth)acrylic ester with at least one compound comprising at least one OH group in the presence of a heterogeneous catalyst comprising at least one inorganic salt. The invention further relates to the use of the (meth)acrylic esters prepared.

(Meth)acrylic acid in the context of the present invention is understood to mean acrylic acid and/or methacrylic acid, and (meth)acrylic esters to mean acrylic esters and/or methacrylic esters. (Meth)acrylic esters are also referred to hereinafter as (meth)acrylates.

Radiation-curable binders based on monomeric and oligomeric (meth)acrylates, by virtue of their solvent-free and easy processability, have found increasing interest from the market as paint resins, which are used especially for dispersions. There is therefore a continuing need for improved preparation processes for (meth)acrylates.

(Meth)acrylates are prepared usually by catalytic esterification of (meth)acrylic acid or transesterification of other (meth)acrylic esters with alcohols. The reaction product typically comprises the desired (meth)acrylate in the (meth) acrylic acid used as the reactant or the (meth)acrylic ester used as the reactant and possibly alcoholic by-products.

Different catalysts can be used for preparation of (meth) acrylic esters. DE 27 44 641 A1 discloses, for example, lithium hydroxide as a catalyst. However, alkali metals and alkali metal hydroxides are hydrolyzed even at a low water content and therefore require anhydrous reaction conditions. EP-A 1 236 994 describes the preparation of ureido(meth) acrylates by transesterification of (meth)acrylate in the presence of titanium alkoxides or 1,3-dicarbonyl chelates of titanium, zirconium, iron or zinc.

A disadvantage of these compounds is that the metal compounds are moisture-sensitive and are therefore deactivated easily. In addition, traces of the catalysts remaining in the product influence any subsequent polymerization, and therefore have to be removed from the product in a complex manner. Such a removal is usually performed by means of an aqueous wash, and so the product subsequently has to be dried.

WO 2006/012980 describes the preparation of (meth)acrylates of cyclic or open-chain N-hydroxyalkylated amides, wherein (meth)acrylic acid is esterified or at least one (meth) acrylic ester is transesterified in the presence of a heterogeneous catalyst composed of inorganic salts. One inorganic salt used is $K_3PO_4$ in anhydrous form. A disadvantage of this is that anhydrous $K_3PO_4$ reacts very rapidly to form by-products.

U.S. Pat. No. 7,528,278 describes a transesterification process which uses a mixture of inorganic salts as a heterogeneous catalyst, the transesterification process being performed especially in the presence of a mixture of potassium carbonate and potassium chloride. Using this catalyst, the reaction can still afford adequate conversions up to a water content of 3000 ppm based on the total weight of the reaction mixture. However, the reaction with potassium carbonate can proceed much more slowly than with potassium phosphate.

In spite of the extensive prior art in the field of preparation of (meth)acrylates, there is a constant need for optimization in order to make the chemical processes more efficient by higher yields and at the same time to provide light-colored esterification products which find use, for example, in dispersions.

It is an object of the present invention to provide a simple process with which light-colored esterification products are preparable in good yield. More particularly, the proportion of poly(meth)acrylated products shall be suppressed.

The object is achieved by a process for preparing (meth) acrylic esters by esterifying (meth)acrylic acid or transesterifying at least one (meth)acrylic ester with at least one compound comprising at least one OH group in the presence of a heterogeneous catalyst comprising at least one inorganic salt, wherein the esterification or transesterification is performed in the presence of 300 to 3000 ppm of water based on the total weight of the reaction mixture.

It has been found that, surprisingly, in the preparation of (meth)acrylates, the addition of the inventive amount of water increases the selectivity. In addition, by virtue of the process according to the invention, polymer formation is reduced and the esterification products obtained have a good color number.

In the context of the invention, ppm based on the total weight of the reaction mixture means one part by mass in one million and can be reported in milligrams per kilogram.

In this context, the reaction mixture comprises both the reactants and any assistants, for example solvents or polymerization inhibitors. Hereinafter, ppm should be understood, unless specified otherwise, as ppm based on the total weight of the reaction mixture.

According to the invention, the esterification or the transesterification is performed in the presence of 300 to 3000 ppm of water, preferably 400 to 2000 ppm of water. Particular preference is given to 500 to 1200 ppm of water, for example 800 ppm.

In the context of this document, water comprises essentially $H_2O$ and is present in the liquid state. "Essentially $H_2O$" means that the water comprises at least 95% (based on the weight of the water), preferably at least 99% (based on the weight of the water) of $H_2O$.

The water may additionally comprise a typical proportion of impurities, which may be less than 5% (based on the weight of the water), preferably less than 1%. The impurities present in the water may be one or more of the following compounds in undissolved or dissolved form:

- inorganic compounds, for example salts and minerals, which by way of example may comprise the following ions:
  - cations: sodium, potassium, magnesium, calcium, iron, aluminum;
  - anions: chloride, iodide, bromide, sulfite, sulfide, sulfate, carbonate, fluoride, phosphate, silicate, nitrate, nitrite;
- organic compounds and
- microorganisms.

When the reaction mixture is made up, the water can be added completely in any process step. Alternatively, water can be added in portions in several process steps, such that the desired total amount of water is present in total. Typically, in a first process step, when the reaction mixture is made up, (meth)acrylic acid or at least one (meth)acrylic ester and optionally polymerization inhibitors and optionally solvent are initially charged. In a next process step, this mixture can be heated if required. This is followed by the addition of the compounds comprising at least one OH group and of the heterogeneous catalyst. This mixture constitutes the starting mixture for esterification of (meth)acrylic acid or transesterification of at least one (meth)acrylic ester.

The water can be supplied completely or in portions in one process step before or after addition of the heterogeneous catalyst. Preference is given to the complete addition of the water before the addition of the heterogeneous catalyst, more preferably before the addition of the alcohol.

The catalysts used in accordance with the invention have a small tendency to be deactivated under the influence of the amount of water determined in accordance with the invention. Suitable for this purpose are especially inorganic salts which are sufficiently basic to catalyze esterification or transesterification, and in combination with the inventive amount of water suppress side reactions, for example the Michael reaction.

The heterogeneous catalyst may be in anhydrous form. In this way, precise metered addition of the water can be achieved. Alternatively, a portion of the water may be present in the heterogeneous catalyst and this portion may be bound in the heterogeneous catalyst, for example, as water of crystallization. The portion of the water present in the heterogeneous catalyst can be taken into account in the metered addition of the amount of water.

The heterogeneous catalyst may comprise up to 10% by weight of water based on the total weight of the catalyst.

Heterogeneous catalysts in the context of the invention are those which have a solubility in the reaction mixture at 25° C. of not more than 1 g/l, preferably of not more than 0.5 g/l and more preferably of not more than 0.25 g/l.

Inorganic salts usable in accordance with the invention are those which have a $pK_B$ of not more than 7.0, preferably of not more than 6.1 and more preferably of not more than 4.0. At the same time, the $pK_B$ should not be less than 1.0, preferably not less than 1.5 and more preferably not less than 1.6.

The inorganic salt preferably has at least one anion selected from the group consisting of carbonate ($CO_3^{2-}$), hydrogencarbonate ($HCO_3^-$), phosphate ($PO_4^{3-}$), hydrogenphosphate ($HPO_4^{2-}$), dihydrogenphosphate ($H_2PO_4^-$), sulfate ($SO_4^{2-}$), sulfite ($SO_3^{2-}$) and carboxylate ($RCOO^-$) in which R is $C_1$-$C_{18}$-alkyl or $C_2$-$C_{18}$-alkyl optionally interrupted by one or more oxygen and/or sulfur atoms and/or one or more substituted or unsubstituted imino groups, or $C_6$-$C_{12}$-aryl.

Preference is given to carbonate and phosphate, particular preference to phosphate.

Phosphate is also understood to mean the condensation products, for example biphosphates, triphosphates and polyphosphates.

The inorganic salt preferably has at least one cation selected from the group consisting of alkali metals, alkaline earth metals, ammonium, cerium, iron, manganese, chromium, molybdenum, cobalt, nickel or zinc.

Preference is given to alkali metals and particular preference to lithium, sodium or potassium.

Particularly preferred inorganic salts are $Li_3PO_4$, $K_3PO_4$, $Na_3PO_4$, $K_2CO_3$ and $Na_2CO_3$ and hydrates thereof, very particular preference being given to $K_3PO_4$.

(Meth)acrylates may be (meth)acrylic acid or esters of (meth)acrylic acid with a saturated alcohol, preferably saturated $C_1$-$C_{10}$-alkyl esters of (meth)acrylic acid, more preferably saturated $C_1$-$C_4$-alkyl esters of (meth)acrylic acid.

In the context of the invention, "saturated" means compounds without C—C multiple bonds (excluding of course the C=C double bond in the (meth)acryloyl units).

Examples of compounds are methyl, ethyl, n-butyl, isobutyl, tert-butyl, n-octyl and 2-ethylhexyl (meth)acrylate, 1,2-ethylene glycol di- and mono(meth)acrylate, 1,4-butanediol di- and mono(meth)acrylate, 1,6-hexanediol di- and mono (meth)acrylate, trimethylolpropane tri(meth)acrylate and pentaerythrityl tetra(meth)acrylate.

Particular preference is given to methyl, ethyl, n-butyl and 2-ethylhexyl (meth)acrylate, very particular preference to methyl, ethyl and n-butyl (meth)acrylate, particularly to methyl and ethyl (meth)acrylate and especially to methyl (meth)acrylate.

Useful compounds having one or more OH group(s) are especially N-hydroxyalkylated amides. N-Hydroxyalkylated amides in the context of the invention are those compounds which have at least one $Z^1$—(C=O)—N— group and at least one hydroxyl group (—OH), where the hydroxyl group is bonded to the nitrogen atom of the $Z^1$—(C=O)—N— group and $Z^1$ is as defined below. The N-hydroxyalkylated amides may be cyclic (C)N-hydroxyalkylated amides

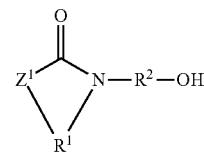

or open-chain (O)N-hydroxyalkylated amides

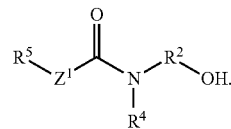

In this context:

$Z^1$ is oxygen, sulfur, unsubstituted or substituted phosphorus or unsubstituted or monosubstituted nitrogen (N—$R^3$), $R^1$ and $R^2$ are each independently $C_2$-$C_{20}$-alkylene, $C_5$-$C_{12}$-cycloalkylene, $C_6$-$C_{12}$-arylene, or $C_2$-$C_{20}$-alkylene interrupted by one or more oxygen and/or sulfur atoms and/or one or more substituted or unsubstituted imino groups and/or by one or more cycloalkyl, —(CO)—, —O(CO)O—, —(NH)(CO)O—, —O(CO)(NH)—, —O(CO)— or —(CO)O— groups, where the radicals mentioned may each be substituted by aryl, alkyl, aryloxy, alkyloxy, heteroatoms and/or heterocycles, or $R^2$—OH is a group of the formula —$[X_i]_k$—H, $R^3$, $R^4$ and $R^5$ are each independently hydrogen, $C_1$-$C_{18}$-alkyl, $C_2$-$C_{18}$-alkyl optionally interrupted by one or more oxygen and/or sulfur atoms and/or one or more substituted or unsubstituted imino groups, $C_2$-$C_{18}$-alkenyl, $C_6$-$C_{12}$-aryl, $C_5$-$C_{12}$-cycloalkyl or a five- to six-membered heterocycle having oxygen, nitrogen and/or sulfur atoms, where the radicals mentioned may each be substituted by aryl, alkyl, aryloxy, alkyloxy, heteroatoms and/or heterocycles, where $R^3$ and $R^5$ may also together form a five- to twelve-membered ring, with the proviso that, in the case that $Z^1$=O, $R^5$ is only unsubstituted $C_1$-$C_{18}$-alkyl, $C_6$-$C_{12}$-aryl or $C_5$-$C_{12}$-cycloalkyl, k is a number from 1 to 50 and $X_i$ for each i=1 to k may independently be selected from the group of —$CH_2$—$CH_2$—O—, —$CH_2$—$CH_2$—N(H)—, —$CH_2$—$CH_2$—$CH_2$—N(H)—, —$CH_2$—CH($NH_2$)—, —$CH_2$—CH(NHCHO)—, —$CH_2$—CH($CH_3$)—O—, —CH($CH_3$)—$CH_2$—O—, —$CH_2$—C($CH_3$)$_2$—O—, —C($CH_3$)$_2$—$CH_2$—O—, —$CH_2$—$CH_2$—$CH_2$—O—, —$CH_2$—$CH_2$—$CH_2$—$CH_2$—O—, —$CH_2$—CHVin-O—, —CHVin-$CH_2$—O—, —$CH_2$—CHPh-O and —CHPh-$CH_2$—O—, in which Ph is phenyl and Vin is vinyl.

In the above definitions, $C_2$-$C_{20}$-alkylene optionally substituted by aryl, alkyl, aryloxy, alkyloxy, heteroatoms and/or heterocycles is, for example, 1,2-ethylene, 1,2-propylene, 1,3-propylene, 1,4-butylene, 1,6-hexylene, 2-methyl-1,3-propylene, 2-ethyl-1,3-propylene, 2,2-dimethyl-1,3-propylene, 2,2-dimethyl-1,4-butylene, $C_5$-$C_{12}$-cycloalkylene optionally substituted by aryl, alkyl, aryloxy, alkyloxy, heteroatoms and/or heterocycles is, for example, cyclopropylene, cyclopentylene, cyclohexylene, cyclooctylene, cyclododecylene, $C_2$-$C_{20}$-alkylene optionally substituted by aryl, alkyl, aryloxy, alkyloxy, heteroatoms and/or heterocycles and interrupted by one or more oxygen and/or sulfur atoms and/or one or more substituted or unsubstituted imino groups and/or by one or more cycloalkyl, —(CO)—, —O(CO)O—, —(NH)(CO)O—, —O(CO)(NH)—, —O(CO)— or —(CO)O— groups is, for example, 1-oxa-1,3-propylene, 1,4-dioxa-1,6-hexylene, 1,4,7-trioxa-1,9-nonylene, 1-oxa-1,4-butylene, 1,5-dioxa-1,8-octylene, 1-oxa-1,5-pentylene, 1-oxa-1,7-heptylene, 1,6-dioxa-1,10-decylene, 1-oxa-3-methyl-1,3-propylene, 1-oxa-3-methyl-1,4-butylene, 1-oxa-3,3-dimethyl-1,4-butylene, 1-oxa-3,3-dimethyl-1,5-pentylene, 1,4-dioxa-3,6-dimethyl-1,6-hexylene, 1-oxa-2-methyl-1,3-propylene, 1,4-dioxa-2,5-dimethyl-1,6-hexylene, 1-oxa-1,5-pent-3-enylene, 1-oxa-1,5-pent-3-inylene, 1,1-, 1,2-, 1,3- or 1,4-cyclohexylene, 1,2- or 1,3-cyclopentylene, 1,2-, 1,3- or 1,4-phenylene, 4,4'-biphenylene, 1,4-diaza-1,4-butylene, 1-aza-1,3-propylene, 1,4,7-triaza-1,7-heptylene, 1,4-diaza-1,6-hexylene, 1,4-diaza-7-oxa-1,7-heptylene, 4,7-diaza-1-oxa-1,7-heptylene, 4-aza-1-oxa-1,6-hexylene, 1-aza-4-oxa-1,4-butylene, 1-aza-1,3-propylene, 4-aza-1-oxa-1,4-butylene, 4-aza-1,7-dioxa-1,7-heptylene, 4-aza-1-oxa-4-methyl-1,6-hexylene, 4-aza-1,7-dioxa-4-methyl-1,7-heptylene, 4-aza-1,7-dioxa-4-(2'-hydroxyethyl)-1,7-heptylene, 4-aza-1-oxa-(2'-hydroxyethyl)-1,6-hexylene or 1,4-piperazinylene, $C_6$-$C_{12}$-arylene optionally substituted by aryl, alkyl, aryloxy, alkyloxy, heteroatoms and/or heterocycles is, for example, 1,2-, 1,3- or 1,4-phenylene, 4,4'-biphenylene, tolylene or xylylene, $C_1$-$C_{18}$-alkyl or $C_2$-$C_{18}$-alkyl optionally interrupted by one or more oxygen and/or sulfur atoms and/or one or more substituted or unsubstituted imino groups, is, for example, methyl, ethyl, propyl, isopropyl, n-butyl, sec-butyl, tert-butyl, pentyl, hexyl, heptyl, octyl, 2-ethylhexyl, 2,4,4-trimethylpentyl, decyl, dodecyl, tetradecyl, hexadecyl, octadecyl, 1,1-dimethylpropyl, 1,1-dimethylbutyl, 1,1,3,3-tetramethylbutyl, benzyl, 1-phenylethyl, 2-phenylethyl, α,α-dimethylbenzyl, benzhydryl, p-tolylmethyl, 1-(p-butylphenyl)ethyl, p-chlorobenzyl, 2,4-dichlorobenzyl, p-methoxybenzyl, m-ethoxybenzyl, 2-cyanoethyl, 2-cyanopropyl, 2-methoxycarbonylethyl, 2-ethoxycarbonylethyl, 2-butoxy-carbonylpropyl, 1,2-di(methoxycarbonyl)ethyl, 2-methoxyethyl, 2-ethoxyethyl, 2-butoxyethyl, diethoxymethyl, diethoxyethyl, 1,3-dioxolan-2-yl, 1,3-dioxan-2-yl, 2-methyl-1,3-dioxolan-2-yl, 4-methyl-1,3-dioxolan-2-yl, 2-isopropoxyethyl, 2-butoxy-propyl, 2-octyloxyethyl, chloromethyl, 2-chloroethyl, trichloromethyl, trifluoromethyl, 1,1-dimethyl-2-chloroethyl, 2-methoxyisopropyl, 2-ethoxyethyl, butylthiomethyl, 2-dodecylthioethyl, 2-phenylthioethyl, 2,2,2-trifluoroethyl, 2-hydroxyethyl, 2-hydroxypropyl, 3-hydroxypropyl, 4-hydroxybutyl, 6-hydroxyhexyl, 2-aminoethyl, 2-aminopropyl, 3-aminopropyl, 4-aminobutyl, 6-aminohexyl, 2-methylaminoethyl, 2-methylaminopropyl, 3-methylaminopropyl, 4-methylaminobutyl, 6-methylaminohexyl, 2-dimethylaminoethyl, 2-dimethylaminopropyl, 3-dimethylaminopropyl, 4-dimethylaminobutyl, 6-dimethylaminohexyl, 2-hydroxy-2,2-dimethylethyl, 2-phenoxyethyl, 2-phenoxypropyl, 3-phenoxypropyl, 4-phenoxybutyl, 6-phenoxyhexyl, 2-methoxyethyl, 2-methoxypropyl, 3-methoxypropyl, 4-methoxybutyl, 6-methoxyhexyl, 2-ethoxyethyl, 2-ethoxypropyl, 3-ethoxypropyl, 4-ethoxybutyl or 6-ethoxyhexyl, $C_2$-$C_{18}$-alkenyl optionally interrupted by one or more oxygen and/or sulfur atoms and/or one or more substituted or unsubstituted imino groups is, for example, vinyl, 1-propenyl, allyl, methallyl, 1,1-dimethylallyl, 2-butenyl, 2-hexenyl, octenyl, undecenyl, dodecenyl, octadecenyl, 2-phenylvinyl, 2-methoxyvinyl, 2-ethoxyvinyl, 2-methoxyallyl, 3-methoxyallyl, 2-ethoxyallyl, 3-ethoxyallyl or 1- or 2-chlorovinyl, $C_6$-$C_{12}$-aryl optionally interrupted by one or more oxygen and/or sulfur atoms and/or one or more substituted or unsubstituted imino groups is, for example, phenyl, tolyl, xylyl, α-naphthyl, β-naphthyl, 4-diphenyl, chlorophenyl, dichlorophenyl, trichlorophenyl, difluorophenyl, methylphenyl, dimethylphenyl, trimethylphenyl, ethylphenyl, diethylphenyl, isopropylphenyl, tert-butylphenyl, dodecylphenyl, methoxyphenyl, dimethoxyphenyl, ethoxyphenyl, hexyloxyphenyl, methylnaphthyl, isopropylnaphthyl, chloronaphthyl, ethoxynaphthyl, 2,6-dimethylphenyl, 2,4,6-trimethylphenyl, 2,6-dimethoxyphenyl, 2,6-dichlorophenyl, 4-bromphenyl, 2- or 4-nitrophenyl, 2,4- or 2,6-dinitrophenyl, 4-dimethylaminophenyl, 4-acetylphenyl, methoxyethylphenyl or ethoxymethylphenyl, $C_5$-$C_{12}$-cycloalkyl optionally interrupted by one or more oxygen and/or sulfur atoms and/or one or more substituted or unsubstituted imino groups is, for example, cyclopentyl, cyclohexyl, cyclooctyl, cyclododecyl, methylcyclopentyl, dimethylcyclopentyl, methylcyclohexyl, dimethylcyclohexyl, diethylcyclohexyl, butylcyclohexyl, methoxycyclohexyl, dimethoxycyclohexyl, diethoxycyclohexyl, butylthiocyclohexyl, chlorocyclohexyl, dichlorocyclohexyl, dichlorocyclopentyl and a saturated or unsaturated bicyclic system, for example norbornyl or norbornenyl, and a five- to six-membered heterocycle having oxygen, nitrogen and/or sulfur atoms and optionally interrupted by one or more oxygen and/or sulfur atoms and/or one or more substituted or unsubstituted imino groups is, for example, furyl, thiophenyl, pyrryl, pyridyl, indolyl, benzoxazolyl, dioxolyl, dioxyl, benzimidazolyl, benzthiazolyl, dimethylpyridyl, methylquinolyl, dimethylpyrryl, methoxyfuryl, dimethoxypyridyl, difluoropyridyl, methylthiophenyl, isopropylthiophenyl or tert-butylthiophenyl.

Examples of $R^1$ are 1,2-ethylene, 1,2-propylene, 1,1-dimethyl-1,2-ethylene, 1-hydroxy-methyl-1,2-ethylene, 2-hydroxy-1,3-propylene, 1,3-propylene, 1,4-butylene, 1,6-hexylene, 2-methyl-1,3-propylene, 2-ethyl-1,3-propylene, 2,2-dimethyl-1,3-propylene and 2,2-dimethyl-1,4-butylene, 1,2-cyclopentylene, 1,3-cyclopentylene, 1,2-cyclohexylene, 1,3-cyclohexylene and ortho-phenylene. Preference is given to 1,2-ethylene, 1,2-propylene, 1,3-propylene, particular preference to 1,2-ethylene and 1,2-propylene and very particular preference to 1,2-ethylene.

Examples of $R^2$ are 1,2-ethylene, 1,2-propylene, 1,1-dimethyl-1,2-ethylene, 1-hydroxy-methyl-1,2-ethylene, 2-hydroxy-1,3-propylene, 1,3-propylene, 1,4-butylene, 1,6-hexylene, 2-methyl-1,3-propylene, 2-ethyl-1,3-propylene, 2,2-dimethyl-1,3-propylene and 2,2-dimethyl-1,4-butylene, 1,2-cyclopentylene, 1,3-cyclopentylene, 1,2-cyclohexylene, 1,3-cyclohexylene and ortho-phenylene. Preference is given to 1,2-ethylene, 1,2-propylene, 1,3-propylene, particular preference to 1,2-ethylene and 1,2-propylene and very particular preference to 1,2-ethylene.

Examples of $R^3$ and $R^5$ are each independently hydrogen or $C_1$-$C_4$-alkyl, which in the context of the present invention is methyl, ethyl, isopropyl, n-propyl, n-butyl, isobutyl, sec-butyl or tert-butyl, preferably hydrogen, methyl, ethyl, n-propyl and n-butyl, more preferably hydrogen, methyl, ethyl and n-butyl, and even more preferably hydrogen, methyl and ethyl, and especially hydrogen.

When $R^3$ and $R^5$ form a common ring, $R^3$ and $R^5$ together may be 1,4-butylene, 1,5-pentylene or 3-oxa-1,5-pentylene.

Examples of $R^4$ are hydrogen, methyl, ethyl, isopropyl, n-propyl, n-butyl, isobutyl, sec-butyl, tert-butyl, n-hexyl, n-heptyl, n-octyl, n-decyl, n-dodecyl, n-tetradecyl, n-hexadecyl, n-octadecyl, n-eicosyl, 2-ethylhexyl, cyclopentyl, cyclohexyl, cyclooctyl, cyclododecyl, phenyl, naphthyl or benzyl.

$Z^1$ is preferably O or $NR^3$, more preferably $NR^3$.

Preference is given to the cyclic amides (C) over the open-chain (O) amides.

Preferred cyclic amides (C) are 2'-hydroxyethylethyleneurea, 3'-hydroxypropylethyleneurea, 2'-hydroxypropylethyleneurea, 2'-hydroxyethyl-1,3-propyleneurea, 2'-hydroxypropyl-1,3-propyleneurea, 3'-hydroxypropyl-1,3-propyleneurea, 2'-hydroxyethyl-1,2-propyleneurea, 2'-hydroxypropyl-1,2-propyleneurea, 3'-hydroxypropyl-1,2-propyleneurea, 1-(2'-hydroxyethyl)imidazolidine-2,4-dione, 1-(2'-hydroxyethyl)dihydropyrimidine-2,4-dione or 3-(2-hydroxyethyl)-oxazolidin-2-one. Particular preference is given to 2'-hydroxyethylethyleneurea, 3'-hydroxypropylethyleneurea, 2'-hydroxyethyl-1,3-propyleneurea and 3'-hydroxypropyl-1,3-propyleneurea.

Preferred open-chain amides are N-(2-hydroxyethyl)urea, N-(2-hydroxypropyl)urea, N-(3-hydroxypropyl)urea, N',N'-dimethyl-N-(2-hydroxyethyl)urea, N',N'-dimethyl-N-(2-hydroxypropyl)urea, N',N'-dimethyl-N-(3-hydroxypropyl)urea, N,N'-diethyl-N-(2-hydroxyethyl)urea, N',N'-diethyl-N-(2-hydroxypropyl)urea, N',N'-diethyl-N-(3-hydroxypropyl)urea, N',N'-di-n-butyl-N-(2-hydroxyethyl)urea, N',N'-di-n-butyl-N-(2-hydroxypropyl)urea and N',N'-di-n-butyl-N-(3-hydroxypropyl)urea, particular preference being given to N-(2-hydroxyethyl)urea, N-(2-hydroxypropyl)urea and N-(3-hydroxypropyl)urea.

The esterification with (meth)acrylic acid or preferably the transesterification of the amide (C) or (O) is effected with at least one, preferably one, (meth)acrylate in the presence of at least one heterogeneous catalyst comprising at least one inorganic salt, preferably one inorganic salt.

The process according to the invention is more preferably suitable for preparation of ureido(meth)acrylates by transesterification of (meth)acrylate. Ureido alcohols in the context of the present document are those compounds which have at least one N—(C=O)—N— group and at least one hydroxyl group (—OH).

Typical by-products of the reaction of cyclic or open-chain N-hydroxyalkylated amides in which $Z^1$ is N—H with (meth)acrylic acid or (meth)acrylic esters are the (meth)acrylamide bonded via this nitrogen atom, the addition product, joined via this nitrogen atom, onto the double bond of the reactant (meth)acrylate or of the ureido(meth)acrylate, the addition product, joined via the free hydroxyl group, onto the double bond of the reactant (meth)acrylate or of the ureido(meth)acrylate, and products which result from intra- or intermolecular elimination of the $R^5$—$Z^1$ group from the cyclic or open-chain N-hydroxyalkylated amides, which can then in turn be esterified or transesterified.

The catalyzed esterification or transesterification is effected generally at a temperature of the reaction mixture of 30 to 140° C., preferably at 50 to 120° C., more preferably at 60 to 100° C. and most preferably at 60 to 90° C.

The reaction can optionally be performed under a gentle vacuum of, for example, 300 mbar to standard pressure if the water released in the esterification or the low-boiling alcohol formed in the transesterification is to be distilled off, optionally as an azeotrope.

The molar ratio between (meth)acrylic acid or (meth)acrylic ester and alcohol (C) or (O) in the esterification or transesterification catalyzed by an inorganic salt in the presence of the amount of water determined in accordance with the invention is generally 1 to 30:1 mol/mol, preferably 1.5 to 20:1 mol/mol and more preferably 2 to 10:1 mol/mol.

The content of inorganic salts in the reaction mixture is generally in the range from about 0.01 to 5 mol %, preferably 0.1 to 1.8 and more preferably 0.5 to 1.5 mol %, based on the sum of the components (C) or (O) used.

In the esterification or transesterification, polymerization inhibitors may be required. In the inventive reaction regime, it is possible to add additional polymerization inhibitors to the reaction mixture over and above the polymerization inhibitors present in the (meth)acrylic ester in any case, examples being hydroquinone monomethyl ether, phenothiazine, phenols, for example 2-tert-butyl-4-methylphenol, 6-tert-butyl-2,4-dimethylphenol, or N-oxyls such as 4-hydroxy-2,2,6,6-tetramethylpiperidine N-oxyl, 4-oxo-2,2,6,6-tetramethylpiperidine N-oxyl or Uvinul® 4040P from BASF SE, or amines such as Kerobit® BPD from BASF SE (N,N'-di-sec-butyl-p-phenylenediamine), for example in amounts of 50 to 2000 ppm.

The presence of oxygenous gases during the reaction catalyzed by an inorganic salt is preferred. Advantageously, the esterificaiton or transesterification is performed in the presence of an oxygenous gas, preferably air or air-nitrogen mixtures.

In the catalyzed esterification or transesterification, the products are generally obtained with a color number (to DIN ISO 53409) below 250 Hazen, preferably below 150 and more preferably below 60.

The reaction can proceed in organic solvents or mixtures thereof, or without addition of solvents. Apart from the water added in accordance with the invention, the mixtures may be substantially anhydrous. Alternatively, the mixtures may have a water content which can be taken into account in the addition of the water and can optionally be lowered azeotropically in the event that the water content is too high.

In addition, the solvents are substantially free of primary and secondary alcohols, i.e. alcohol content below 10% by weight, preferably alcohol content below 5% by weight, more preferably alcohol content below 1% by weight and most preferably alcohol content below 0.5% by weight.

Suitable organic solvents are those known for these purposes, for example tertiary monools such as $C_3$-$C_6$-alcohols, preferably tert-butanol, tert-amyl alcohol, pyridine, poly-$C_1$-$C_4$-alkylene glycol di-$C_1$-$C_4$-alkyl ethers, preferably polyethylene glycol di-$C_1$-$C_4$-alkyl ethers, for example 1,2-dimethoxyethane, diethylene glycol dimethyl ether, polyethylene glycol dimethyl ether 500, $C_1$-$C_4$-alkylene carbonates, especially propylene carbonate, $C_3$-$C_6$-alkyl acetates, especially tert-butyl acetate, tetrahydrofuran (THF), toluene, 1,3-dioxolane, acetone, isobutyl methyl ketone, ethyl methyl ketone, 1,4-dioxane, tert-butyl methyl ether, cyclohexane, methylcyclohexane, toluene, hexane, dimethoxymethane, 1,1-dimethoxyethane, acetonitrile, and the mono- or polyphasic mixtures thereof.

In a particularly preferred embodiment of the transesterification, the reaction is performed in the (meth)acrylic ester used as the reactant. Very particular preference is given to performing the reaction in such a way that the product (C) or (O), after the reaction has ended, is obtained as an about 10 to 80% by weight solution in the (meth)acrylic ester used as the reactant, especially as a 20 to 50% by weight solution.

The reactants are present in dissolved form, suspended as solids or in emulsion in the reaction mixture. The initial concentration of the reactants is preferably in the range from about 0.1 to 20 mol/l, especially 0.15 to 10 mol/l or 0.2 to 5 mol/l.

The reaction can be effected continuously, for example in a tubular reactor or in a stirred reactor cascade, or batchwise.

The reaction can be performed in all reactors suitable for such a reaction. Suitable reactors are known to those skilled in the art. Preference is given to effecting the reaction in a stirred tank reactor or a fixed bed reactor.

Any desired processes can be used for mixing of the mixture. Specific stirrer apparatus is not required. The mixing can be effected, for example, by feeding in a gas, preferably an oxygenous gas (see below). The reaction mixture may be mono- or polyphasic, and the reactants are initially charged dissolved, suspended or emulsified therein. The temperature is adjusted to the desired value during the reaction and can, if desired, be increased or reduced during the course of the reaction.

Water in the case of an esterification, or alcohols which are released from the alkyl(meth)acrylates in a transesterification, are removed continuously or stepwise in a manner known per se, for example distillation under standard pressure or azeotropic removal, stripping, adsorption, pervaporation and diffusion through membranes or extraction.

The stripping can be effected, for example, by passing an oxygenous gas, preferably air or an air-nitrogen mixture, through the reaction mixture, optionally in addition to a distillation.

Preferentially suitable for absorption are molecular sieves or zeolites with a pore size, for example, in the range from about 3 to 10 Å, and removal by distillation or with the aid of suitable semipermeable membranes.

However, it is also possible to supply the removed mixture of alkyl (meth)acrylate and the parent alcohol thereof, which frequently forms an azeotrope, directly into a plant for preparing the alkyl (meth)acrylate, in order to reutilize it therein in an esterification with (meth)acrylic acid.

After the reaction has ended, the product mixture obtained can be used further without further purification, or it can be purified if required in a further step.

In general, the heterogeneous catalyst used is merely removed from the product mixture and the desired reaction product is removed from any organic solvent used.

Any removal of the heterogeneous catalyst is generally effected by filtration, electrofiltration, absorption, centrifugation or decantation, preferably by filtration. The heterogeneous catalyst removed can subsequently be used for further reactions.

The removal of the organic solvent is effected generally by distillation, rectification or, in the case of solid reaction products, by filtration.

For further purification of the reaction product, it is also possible to perform chromatography.

Preference is given, however, to removing merely the heterogeneous catalyst and any solvent used. The reaction conditions in the inventive esterification or transesterification are preferably selected such that the formation of by-products is reduced, which originate, for example, from unwanted free-radical polymerization of the (meth)acrylate used and can otherwise be prevented only by addition of stabilizers.

The (meth)acrylic esters prepared in accordance with the invention find uses, for example, as monomers or comonomers in the preparation of dispersions, for example acrylic dispersions, as reactive diluents, for example in radiation-curable coating materials or in paints, preferably in exterior paints, and in dispersions for use in the papermaking sector, in the cosmetics sector, in the pharmaceutical sector, in agrochemical formulations, in the textile industry and in the oil production sector.

The examples which follow are intended to illustrate the properties of the invention, but without restricting it.

EXAMPLES

The experiments were conducted for a total of four different compositions of the heterogeneous catalyst $K_3PO_4$ (K1, K2, K3, K4).

Catalysts K1, K2, K3 and K4 were analyzed by means of elementary analysis and the results for the compositions thereof are listed in Table 1, the elements being bound in salt form in the catalyst.

TABLE 1

Composition of catalysts K1 to K4 determined by means of elementary analysis

| | $Cl^-$ mg/kg | $S^{2-}$ mg/kg | $Al^{3+}$ mg/kg | $Fe^{2+/3+}$ mg/kg | $K^+$ g/100 g | $Li^+$ mg/kg | $Na^+$ g/100 g | P g/100 g |
|---|---|---|---|---|---|---|---|---|
| K1 | 36 | 25 | <3 | 4 | 52 | <3 | 0.3 | 14 |
| K2 | 34 | 47 | <3 | 4 | 53 | <3 | 0.5 | 14 |
| K3 | 25 | 52 | <3 | 29 | 54 | <3 | 0.23 | 14.4 |
| K4 | 98 | <2 | <3 | 9 | 52 | <3 | 0.26 | 13.5 |

In addition, the particle size of the $K_3PO_4$ catalysts K1, K2 and K3 was determined by means of laser diffraction (Malvern Mastersizer 2000) and of the Scirocco dispersing unit at pressures of 0.5 bar, 1.0 bar and 3.0 bar. The results are reproduced in Table 2.

TABLE 2

Particle size of catalysts K1 to K3, determined by means of laser diffraction.

| | 1 to 10 μm | 10 to 100 μm | 100 to 1000 μm | >1000 μm |
|---|---|---|---|---|
| K1 | 1% | 30% | 70% | 0 |
| K2 | 9% | 53% | 38% | 0 |
| K3 | 2% | 33% | 55% | 10% |

Example 1

Transesterification of MMA Comprising 800 ppm of Water

The transesterification was effected in a 750 mL jacketed reactor equipped with an anchor stirrer, a separating column and a liquid divider. The reflux ratio was 3:1 (reflux:efflux), the stirrer speed (anchor stirrer) 200-250 rpm and the air introduction rate 1.5 L/h.

This apparatus was initially charged with 0.041 g of phenothiazine (PTZ), 0.287 g of methylhydroquinone (MEHQ) (polymerization inhibitors) and 690 g of methyl methacrylate (MMA) at room temperature. The reaction mixture was heated and 130 g of 2-hydroxyethylethyleneurea (HEEH) were added, then the mixture was heated further and the catalyst ($K_3PO_4$, 2.65 g) and 800 ppm of water were added.

Subsequently, a pressure of 450 mbar (abs) was established and the resulting bottom temperature was 73 to 80° C.

The experiments for catalysts K1 to K3 were each conducted with an addition of 800 ppm of water. After an experimental duration of 5 hours, the distillation was shut down and the bottom product was analyzed by gas chromatography (GC) and high-performance liquid chromatography (HPLC) for the ureidomethacrylate (UMA) product, and also unconverted HEEH, by-product I and by-product II.

The secondary components discovered include the bisacrylate formed by formation of the amide by reaction of UMA with a further equivalent of methyl methacrylate (by-product I) and the addition product of the alcohol HEEH used onto the double bond of the desired product (by-product II).

The results are shown in Table 3.

TABLE 3

Results of the transesterification of MMA with HEEH to give UMA in the presence of catalyst K1, K2 or K3, with 800 ppm of water having been supplied to the reaction.

| $K_3PO_4$ | Addition of water (ppm) | HEEH [GC %] | By-product I [GC %] | By-product II [GC %] | UMA [GC %] |
|---|---|---|---|---|---|
| K1 | 800 | 0 | 0.4 | 2.3 | 17.9 |
| K2 | 800 | 0 | 0.5 | 1.8 | 18.9 |
| K3 | 800 | 0 | 0.4 | 1.9 | 19.4 |

Comparative Example 1

Transesterification of MMA without Water

For comparison, the experiments for catalysts K1 to K3 were performed as described in Example 1 without the addition of water. The results of the comparative experiments are listed in Table 4.

TABLE 4

Results of the transesterification of MMA with HEEH to give UMA in the presence of catalyst K1, K2 or K3, with no additional water having been supplied to the reaction.

| $K_3PO_4$ | Addition of water (ppm) | HEEH [GC %] | By-product I [GC %] | By-product II [GC %] | UMA [GC %] |
|---|---|---|---|---|---|
| K1 | 0 | 0 | 0.4 | 5.1 | 15 |
| K2 | 0 | 0 | 0.9 | 6.8 | 15.9 |
| K3 | 0 | 0 | 0.8 | 9.2 | 14.3 |

The comparison of the experiments from Example 1 and Comparative Example 1 shows clearly that the controlled addition of water results in an improved yield over the processes known in the prior art. With a small proportion of the crosslinker and of the by-products, the transesterification proceeds with high selectivity and high conversion.

Example 2

Transesterification of MMA Comprising 800 ppm of Water

The experiments for catalysts K1 and K3 were conducted in a heatable jacketed reactor (capacity 4 L) with an anchor stirrer, a separating column and a liquid divider. The stirrer speed (anchor stirrer) was 160 rpm and the air introduction rate 1.5 L/h.

This apparatus was initially charged with 0.123 g of phenothiazine (PTZ), 0.861 g of methylhydroquinone (MEHQ) (polymerization inhibitors) and 2070 g of MMA at room temperature. The reaction mixture was heated to 70° C., and 390 g of 2-hydroxyethylethyleneurea (HEEH), the catalyst ($K_3PO_4$, 7.95 g) and 800 ppm of water were added. The mixture thus obtained comprised a total of 50 ppm of PTZ, 350 ppm of MEHQ, 20.7 mol of MMA, 3 mol of HEEH, 800 ppm of water and 1.25 mol % (based on HEEH) of $K_3PO_4$. Subsequently, a vacuum of 450 mbar was established and the bottom temperature was increased to 78 to 79° C. until distillation commenced under full reflux. After 30 min, distillate was partially recycled continuously (reflux ratio 3:1).

After an experimental duration of 5 hours, the distillation was shut down and the bottoms were analyzed by means of GC and HPLC for the ureidomethacrylate (UMA) product and secondary components formed. The results of this experiment series are listed in Table 5.

TABLE 5

Results of the transesterification of MMA with HEEH to give UMA in a 4 L reactor, with 800 ppm of water having been supplied to the reaction.

| $K_3PO_4$ | Addition of water [ppm] | HEEH [HPLC %] | By-product I [HPLC %] | By-product II [HPLC %] | UMA [HPLC %] |
|---|---|---|---|---|---|
| K1 | 800 | 5.6 | 0.06 | 0.19 | 15.47 |
| K3 | 800 | 6.02 | 0.06 | 0.18 | 15.13 |

Comparative Example 2

Transesterification of MMA without Water

For comparison, the experiments for catalysts K1 and K3 were conducted as described in Example 2 without the addition of water. The results of the comparative experiments are shown in Table 6.

TABLE 6

Results of the transesterification of MMA with HEEH to give UMA in a 4 L reactor, with no water having been supplied to the reaction.

| $K_3PO_4$ | Addition of water [ppm] | HEEH [HPLC %] | By-product I [HPLC %] | By-product II [HPLC %] | UMA [HPLC %] |
|---|---|---|---|---|---|
| K1 | 0 | 1.73 | 0.23 | 1.02 | 20.61 |
| K3 | 0 | 1.61 | 0.26 | 1.56 | 19.67 |

The comparison of the experiments shows clearly that the controlled addition of water suppresses the proportion of by-products, and the transesterification proceeds with high selectivity.

Example 3

Transesterification of MMA as a Function of Water Content

For catalysts K1, K2, K3 and K4, a test series was conducted as a function of water content. For this purpose, a 4 L jacketed reactor equipped with an anchor stirrer, a separating column and a liquid divider was used. The reflux ratio was 3:1 (reflux:efflux), the stirrer speed (anchor stirrer) 160 rpm and the air introduction rate 1.5 l/h.

In this apparatus, as described in Example 2, PTZ, MEHQ and MMA were initially charged at room temperature, and HEEH, $K_3PO_4$ and in each case different amounts of water in the range from 0 to 2000 ppm were added.

Subsequently, the mixture was heated to jacket temperature 95° C. under air, and a vacuum of 450 mbar and a reflux ratio of 3:1 were established. The azeotrope of MeOH and MMA which formed was distilled off.

After an experimental duration of six hours, the distillation was shut down and the bottoms were analyzed by means of GC and HPLC for the ureidomethacrylate (UMA) product and secondary components formed. The secondary components discovered include the bisacrylate formed by formation of the amide by reaction of UMA with a further equivalent of methyl methacrylate (by-product I) and the addition product of the alcohol HEEH used onto the double bond of the product (by-product II).

In order to show the dependence on the catalyst compositions and the amount of water, the experiments were conducted for four different catalysts K1, K2, K3 and K4, as characterized above, with in each case different amounts of water in the range from 0 to 2000 ppm.

The results after 6 hours for the four catalysts K1, K2, K3 and K4 are shown as a function of the amount of water added in Table 7. Table 7 additionally lists the content of HEEH and UMA in the product for each water content. In addition to the by-products and the crosslinker, Table 7 includes the proportion of HEEH converted (in %), the potassium content (in ppm) and the color number (in Hazen).

The results in Table 7 show clearly that the addition of water in the range from 500 to 1500 ppm for each catalyst K1 to K4 leads to an increased conversion of UMA. The proportions of crosslinker and by-products and the potassium content are also reduced within this range. In addition, the experiments show that the process proposed in accordance with the invention enables the preparation of light-colored products with color numbers between 40 and 65 Hazen.

TABLE 7

Results of the transesterification of MMA with HEEH to give UMA for the four catalysts K1, K2, K3 and K4 as a function of the addition of water.

| # | $K_3PO_4$ | $H_2O$ addition [ppm] | HEEH 6 h [HPLC %] | UMA 6 h [HPLC %] | HEEH conversion 6 h [%] | By-product I 6 h [%] | By-product II 6 h [%] | K content [ppm] | Hazen color number |
|---|---|---|---|---|---|---|---|---|---|
| Catalyst 1 | | | | | | | | | |
| 1 | K1 | 0 | 0.3 | 28.1 | 98.9 | 3.5 | 1.1 | 180 | 104 |
| 2 | K1 | 500 | 0.4 | 29.7 | 98.7 | 3.1 | 1.1 | 190 | 81 |
| 3 | K1 | 1000 | 1.2 | 30.1 | 96.2 | 2 | 0.5 | 225 | 50 |
| 4 | K1 | 1500 | 0.2 | 27.7 | 99.3 | 3 | 0.9 | 140 | 220 |
| 5 | K1 | 2000 | 4 | 27.1 | 87.1 | 0.8 | 0.2 | 320 | 53 |
| Catalyst 2 | | | | | | | | | |
| 6 | K2 | 0 | 0.2 | 26.6 | 99.3 | 4.4 | 1.5 | 150 | 65 |
| 7 | K2 | 500 | 1.9 | 30.9 | 94.2 | 1.7 | 0.4 | 165 | 40 |
| 8 | K2 | 1000 | 1.9 | 28 | 93.6 | 1.4 | 0.4 | 200 | 47 |
| 9 | K2 | 1500 | 1.5 | 30.7 | 95.3 | 1.8 | 0.5 | 205 | 76 |
| 10 | K2 | 2000 | 1.8 | 29.6 | 94.3 | 1.6 | 0.5 | 235 | 126 |
| Catalyst 3 | | | | | | | | | |
| 11 | K3 | 0 | 0.1 | 24.7 | 99.6 | 7.6 | 2.2 | 165 | 116 |
| 12 | K3 | 1000 | 0.4 | 30.4 | 98.7 | 3.4 | 1.1 | 165 | 63 |
| 13 | K3 | 2000 | 2.6 | 29.8 | 92.0 | 1.2 | 0.3 | 240 | 58 |
| Catalyst 4 | | | | | | | | | |
| 14 | K4 | 0 | 0.1 | 26.4 | 99.6 | 5.5 | 1.6 | 140 | 49 |
| 15 | K4 | 1000 | 1.0 | 28.6 | 96.6 | 2 | 0.6 | 165 | 52 |
| 16 | K4 | 2000 | 4.5 | 25.8 | 85.1 | 0.8 | 0.2 | 290 | 76 |

The invention claimed is:

1. A process for preparing a (meth)acrylic ester by esterifying (meth)acrylic acid or transesterifying at least one (meth)acrylic ester with at least one compound comprising at least one OH group in the presence of a heterogeneous catalyst consisting of one or more inorganic salts selected from the group consisting of $K_3PO_4$, $Na_3PO_4$, $K_2CO_3$ and $Na_2CO_3$ and hydrates thereof, which comprises performing the esterification or transesterification in the presence of 300 to 3,000 ppm of water based on the total weight of the reaction mixture.

2. The process according to claim 1, wherein the esterification or transesterification is performed in the presence of 400 to 2,000 ppm of water based on the total weight of the reaction mixture.

3. The process according to claim 1, wherein the esterification or transesterification is performed in the presence of 500 to 1,200 ppm of water based on the total weight of the reaction mixture.

4. The process according to claim 1, wherein the water is added completely or in portions in several process steps when the reaction mixture is made up.

5. The process according to claim 1, wherein the water is supplied completely in one process step or in portions in several process steps when the reaction mixture is made up, before or after addition of the heterogeneous catalyst.

6. The process according to claim 1, wherein the water is supplied completely in one process step before the addition of the heterogeneous catalyst.

7. The process according to claim 1, wherein the heterogeneous catalyst is present in anhydrous form or is hygroscopic.

8. The process according to claim 1, wherein the compound comprising at least one OH group comprises open-chain or cyclic N hydroxyalkylated amides.

9. The process according to claim 1, wherein the at least one inorganic salt has a pKB of not more than 7.0 and not less than 1.0, and a solubility in the reaction medium at 25° C. of not more than 1 g/l.

10. The process according to claim 1, wherein the product of the transesterification of cyclic amides or open-chain amides is obtained as an about 10 to 80% by weight solution in the (meth)acrylic ester used as the reactant.

11. The method of claim 6, wherein the water is supplied completely in one process step before the addition of the heterogeneous catalyst before the addition of the compound comprising at least one OH group.

12. The method of claim 1 that is an esterification.

13. The method of claim 1 that is a transesterification.

* * * * *